(12) United States Patent
Grace et al.

(10) Patent No.: US 7,289,207 B2
(45) Date of Patent: Oct. 30, 2007

(54) INTEGRATED OPTICAL BIOSENSOR SYSTEM (IOBS)

(75) Inventors: Karen M. Grace, Los Alamos, NM (US); Martin R. Sweet, Los Alamos, NM (US); Roy M. Goeller, Los Alamos, NM (US); Leland Jean Morrison, White Rock, NM (US); Wynne Kevin Grace, Los Alamos, NM (US); Jerome D. Kolar, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 359 days.

(21) Appl. No.: 10/842,750

(22) Filed: May 11, 2004

(65) Prior Publication Data

US 2005/0088648 A1    Apr. 28, 2005

Related U.S. Application Data

(60) Provisional application No. 60/515,071, filed on Oct. 28, 2003.

(51) Int. Cl.
*G01J 3/30* (2006.01)

(52) U.S. Cl. .................................... 356/318
(58) Field of Classification Search ............... 356/318
See application file for complete search history.

(56) References Cited

U.S. PATENT DOCUMENTS 4,447,546 A    5/1984  Hirschfeld 4,558,014 A    12/1985  Hirschfeld (Continued)

FOREIGN PATENT DOCUMENTS

| EP | 0 535 690 | 3/1997 |
|---|---|---|
| WO | WO90/09574 | 8/1990 |

OTHER PUBLICATIONS

Grace et al. "Reagentless Optical Biosensor (ROB) Prototype", http://www.zyn.com/flc/meeting/presentations/Grace.pdf, p. 10.*

(Continued)

*Primary Examiner*—Layla G. Lauchman
*Assistant Examiner*—Kara Geisel
(74) *Attorney, Agent, or Firm*—Milton D. Wyrick (57) ABSTRACT

An optical biosensor has a first enclosure with a pathogen recognition surface, including a planar optical waveguide and grating located in the first enclosure. An aperture is in the first enclosure for insertion of sample to be investigated to a position in close proximity to the pathogen recognition surface. A laser in the first enclosure includes means for aligning and means for modulating the laser, the laser having its light output directed toward said grating. Detection means are located in the first enclosure and in optical communication with the pathogen recognition surface for detecting pathogens after interrogation by the laser light and outputting the detection. Electronic means is located in the first enclosure and receives the detection for processing the detection and outputting information on the detection, and an electrical power supply is located in the first enclosure for supplying power to the laser, the detection means and the electronic means.

20 Claims, 5 Drawing Sheets

U.S. PATENT DOCUMENTS

| | | |
|---|---|---|
| 4,582,809 A | 4/1986 | Block |
| 4,595,833 A | 6/1986 | Sting |
| 4,654,532 A | 3/1987 | Hirschfeld |
| 4,671,938 A | 6/1987 | Cook |
| 4,716,121 A | 12/1987 | Block |
| 4,844,869 A | 7/1989 | Glass |
| 4,852,967 A | 8/1989 | Cook |
| 4,909,990 A | 3/1990 | Block |
| 5,061,857 A | 10/1991 | Thompson |
| 5,152,962 A | 10/1992 | Lackie |
| 5,242,797 A | 9/1993 | Hirschfeld |
| 5,290,398 A | 3/1994 | Feldman |
| 5,359,681 A | 10/1994 | Jorgenson |
| 5,399,866 A | 3/1995 | Feldman |
| 5,430,813 A | 7/1995 | Anderson |
| 5,442,448 A | 8/1995 | Knoll |
| 5,468,606 A | 11/1995 | Bogart |
| 5,492,674 A | 2/1996 | Meserol |
| 6,136,611 A | 10/2000 | Saaski |
| 6,297,059 B1 | 10/2001 | Song |
| 2005/0154277 A1* | 7/2005 | Tang et al. ................ 600/407 |

OTHER PUBLICATIONS

Yang et al. "A Novel Integrated Optical Sensor for DNA Arrays Detection", SPIE vol. 4092, pp. 155-157.*

Daniel Kelly, "Integrated Optical Biosensor," U.S. Appl. No. 09/598,882, filed Jun. 21, 2000.

Xuedong Song, John Nolan, and Basil Swanson, "Optical Biosensor Based On Fluorescence Resonance Energy Transfer: Ultrasensitive and Apecific Detection Of Protein Toxins," J. Am. Chem., vol. 120, pp. 11514-11515, 1998.

Karen Grace and Basil Swanson, "ROB: Reagentless Optical Biosensor," 2003 R&D, 100 Entry, pp. 1-17, Mar. 1, 2003.

* cited by examiner

INTEGRATED OPTICAL BIOSENSOR SYSTEM (IOBS)

RELATED APPLICATIONS

This application claims the benefit of U.S. provisional patent application Ser. No. 60/515,071 filed Oct. 28, 2003.

The present invention relates to biosensors and more specifically to biosensors that are portable, are simple to use and operate, and cost much less than current biosensors available on the market. This invention was made with Government support under Contract No. W-7405-ENG-36 awarded by the U.S. Department of Energy. The Government has certain rights in the invention.

FIELD OF THE INVENTION

Background of the Invention

Biosensors are devices that detect chemical or biological species with high selectivity on the basis of molecular recognition. Biosensor technology has grown rapidly over the last several years, and incorporates technological improvements in a variety of disciplines, including biochemical methodologies (e.g., organic synthesis, molecular biology) and electronics. The potential market for application of biosensor technology is enormous and includes detection and diagnostics in the health care industry and environmental monitoring.

Although biosensor systems are available for the detection of various bacteria, toxins, and viruses, the devices themselves can be difficult to operate, very expensive, and generally not portable. However, immunochromatographic assays can be taken in the field using test strips sometimes called "smart tickets." These test strips, currently manufactured by Tetracore, Inc., currently located at 11 Firstfield Road, Suite C, Gaithersburg, Md. 20878, and Alexeter currently located in Chicago, Ill. area, and others, are relatively simple to use by placing a sample onto a test strip. If the sample has a sufficiently high concentration of a pathogen, the results can be observed by sight. However, if the pathogen concentration is lower, the results must be read by a relatively large instrument, usually at a base location. These assays are not very sensitive or accurate, as they suffer from problems with cross reactivity, resulting in a high rate of false positives.

The operations required to use the conventional biosensor systems typically involve multiple steps that are very precise and intricate. For example, the biosensor operations may require washing the sample multiple times, followed by mixing several different reagents with the sample; all at precise times and in precise amounts. These processes provide opportunities for the introduction of errors and, thus, the biosensor results are prone to error. The processes also require time to complete and may take up to a few days to yield results. In some cases, for instance with Hantavirus infection, the time required for detection may be longer than the minimum time required to administer successful treatment. In fact, the diagnosis may arrive too late for any type of treatment to be effective.

Currently, there are only a few small, hand-held biosensor systems available for field-testing, such as the previously described test strips. Often, test samples must be brought into the lab from the field or from a remote location. Not only does the transportation take time, which may be very limited, but also the process of transportation may contaminate the sample. Often, the sample itself may present a potential health hazard to those transporting it. In some cases, it may not be possible to transport the sample to a laboratory, such as during combat or in other emergency situations.

Additionally, conventional biosensors systems often require highly trained personnel to operate them, although the above-described test strips are relatively simple to use, they suffer from certain problems. Only very highly skilled personnel are able to perform the chemical processes involved in preparing and analyzing the samples that are required to complete the testing using these systems. The amount of skill required limits the number of potential biosensor system operators. In emergencies, there may be fewer personnel available to operate the equipment and perform the testing. Therefore, the lack of trained personnel available to analyze the samples can become a bottleneck to rapid turnaround times when timely results are imperative.

U.S. Pat. No. 6,136,611 entitled, "Assay Methods and Apparatus", issued Oct. 24, 2000, to Saaski et al., describes an optical assay apparatus that includes a light source module and an optical sensing element coupled by an interrogation module. The light source module produces light having propagation angles ranging from a lower, non-zero limit. This is accomplished by including an obscuration that blocks low propagation angle light. The sensing element includes a reflector portion and a sensing fiber portion. The reflector portion receives, as incident light, the light produced by the light source module and produces, as reflected light, light having an approximately constant propagation angle, preferably just less than the critical angle of the sensing fiber. The sensing element also includes a lens position that collimates signal recovery light collected by the sensing fiber. The interrogation module includes a window containing a light source optical fiber that transmits light from the light source module to the sensing element. The light source fiber has an angled end with a reflective surface to form a right-angle reflector and is embedded within the window in a slot containing an opaque material for absorbing back-scattered light. The sensing fiber may be appropriately adapted for evanescent-wave or surface plasmon resonance sensing operations.

Although the apparatus described in patent '611 provides a method for detecting certain biological material, the apparatus itself has not been optimized to provide a simplistic method of operation. There are still several complex steps in the process that require an expert's attention in order to render accurate results. For example, the sample cell used in the testing process must be completely dehydrated after the insertion of the sample before testing may begin. There are also several reagents that must be added to the sample for processing. The apparatus described in patent '611 also fails to provide a portable optical biosensor system that may be used in the field as well as in a lab. Finally, the components and materials used in the apparatus described in patent '611 are bulky and expensive. Therefore, the system described in patent '611 does not provide a simple to use, portable, and inexpensive method of testing for the presence of certain biological material in a sample.

Therefore, it is an object of the present invention to provide an integrated optical biosensor apparatus that is simple to operate so that an individual who is not highly technically trained can produce accurate results in a timely manner.

It is another object of this invention to provide an integrated optical biosensor apparatus that is smaller than conventional biosensor systems and that is sufficiently portable to operate in the field and point of care settings.

It is yet another object of this invention to provide an integrated optical biosensor apparatus that is inexpensive to build, purchase, and maintain.

SUMMARY OF THE INVENTION

In order to achieve the objects and purposes of the present invention, and in accordance with its objectives, an optical biosensor comprises a first enclosure with a pathogen recognition surface, including a planar optical waveguide and grating located in the first enclosure. An aperture is in the first enclosure for insertion of sample to be investigated to a position in close proximity to the pathogen recognition surface. A laser in the second enclosure includes means for aligning and means for modulating the laser, the laser having its light output directed toward said grating. Detection means are located in the second enclosure and in optical communication with the pathogen recognition surface for detecting pathogens after interrogation by the laser light and outputting the detection. Electronic means is located in the second enclosure and receives the detection for processing the detection and outputting information on the detection, and an electrical power supply is located in the second enclosure for supplying power to the laser, the detection means and the electronic means.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings.

DESCRIPTION OF THE INVENTION

The present invention provides an apparatus for optically detecting the presence of various biological materials using simple and inexpensive components that yields accurate results quickly and with relatively little human intervention. The invention is most easily understood through reference to the drawings.

Figure 1A:
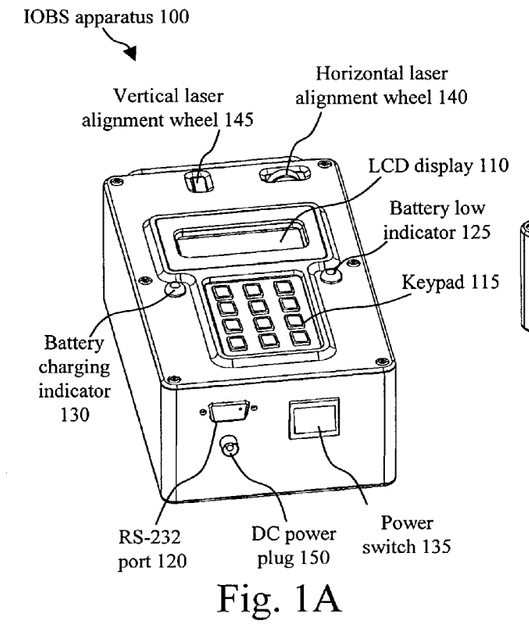
FIG. 1A is an isometric view of a hand-held, portable, integrated optical biosensor apparatus.

FIG. 1A shows an isometric view of an integrated optical biosensor (IOBS) apparatus 100. IOBS apparatus 100 further includes an LCD display 110, a keypad 115, a serial RS-232 port 120 for communication with a PC (not shown), a battery low indicator 125, a battery charging indicator 130, a power switch 135, a horizontal laser alignment wheel 140, a vertical laser alignment wheel 145, and a DC power plug 150.

Figure 1B:
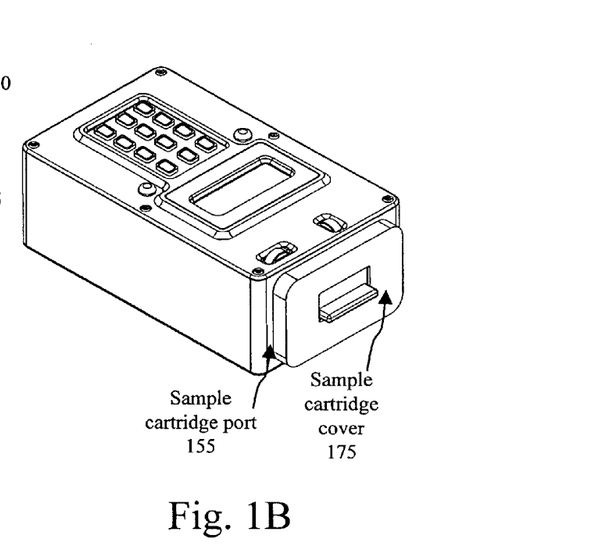
FIG. 1B is a top view of the hand-held, portable, integrated optical biosensor apparatus.

FIG. 1B shows a top view of IOBS apparatus 100 further including a sample cartridge port 155, covered by a sample cartridge cover 175.

Figure 1C:
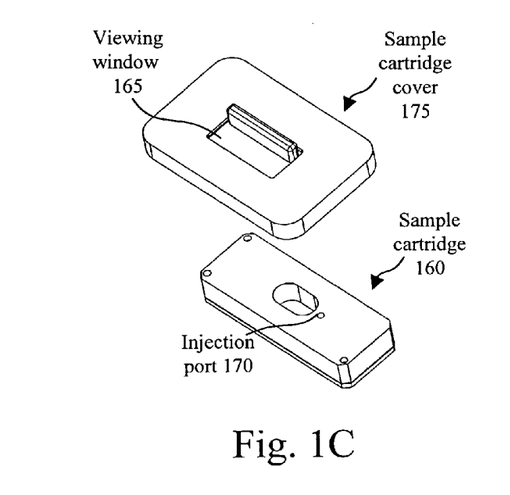
FIG. 1C is an isometric view of a sample cartridge that holds a sample cell for testing and a sample cartridge cover.

FIG. 1C shows a top view of a sample cartridge 160, further including an injection port 170, sample cartridge cover 175, and a viewing window 165. In addition, sample cartridge 160 contains a fluid cell, optical waveguide transducers, a recognition surface, and sample waste reservoir.

The recognition surface (described more specifically below) is deposited onto a planar optical waveguide, which is an optically transparent material that guides light along its length. The optical waveguide has a higher index of refraction than the recognition surface, and than the substrate onto which it is deposited.

Figure 1D:
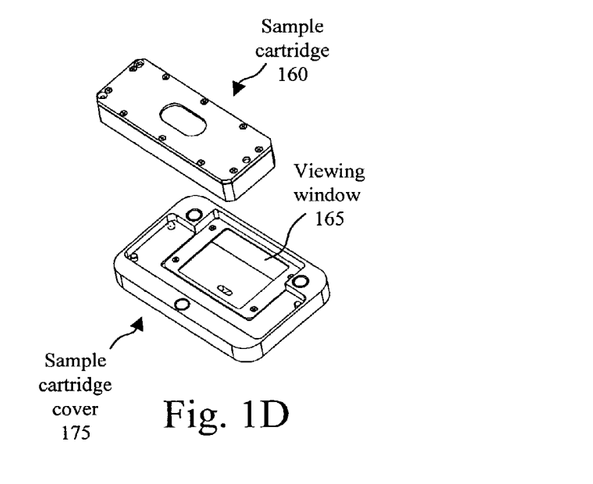
FIG. 1D is a bottom view of the sample cartridge and sample cartridge cover.

FIG. 1D shows a bottom view of sample cartridge 160, sample cartridge cover 175, and viewing window 165. LCD display 110 is a 4-line-by-20-character unit in this example. However, other suitable inexpensive LCD displays are commercially available that would perform adequately. LCD display 110 may also display information from keypad 115 inputs. LCD display 110 has a high-contrast, super-twist, yellow-green screen with a backlight for easy viewing. It may also be used in low light or dark environments, which may be useful in emergencies.

Keypad 115 is a 3-by-4-character keypad containing a matrix keypad of 12 keys. Other types of keypads may be used without changing the spirit of the invention. User inputs to keypad 115 control certain functions of IOBS apparatus 100. A menu-driven program allows the user to select various menu options using keypad 115. For example, after power-up, the user may be asked to enter a number on keypad 115 corresponding to the task he or she wishes to perform, such as calibrating a sample cell, testing a sample, or storing data from a recent test.

RS-232 port 120, battery low indicator 125, battery charging indicator 130, power switch 135, horizontal laser alignment wheel 140, vertical laser alignment wheel 145, DC power plug 150, sample cartridge port 155, viewing window 165, injection port 170, and sample cartridge cover 175 are functionally described with reference to FIGS. 2 and 3.

Figure 2:
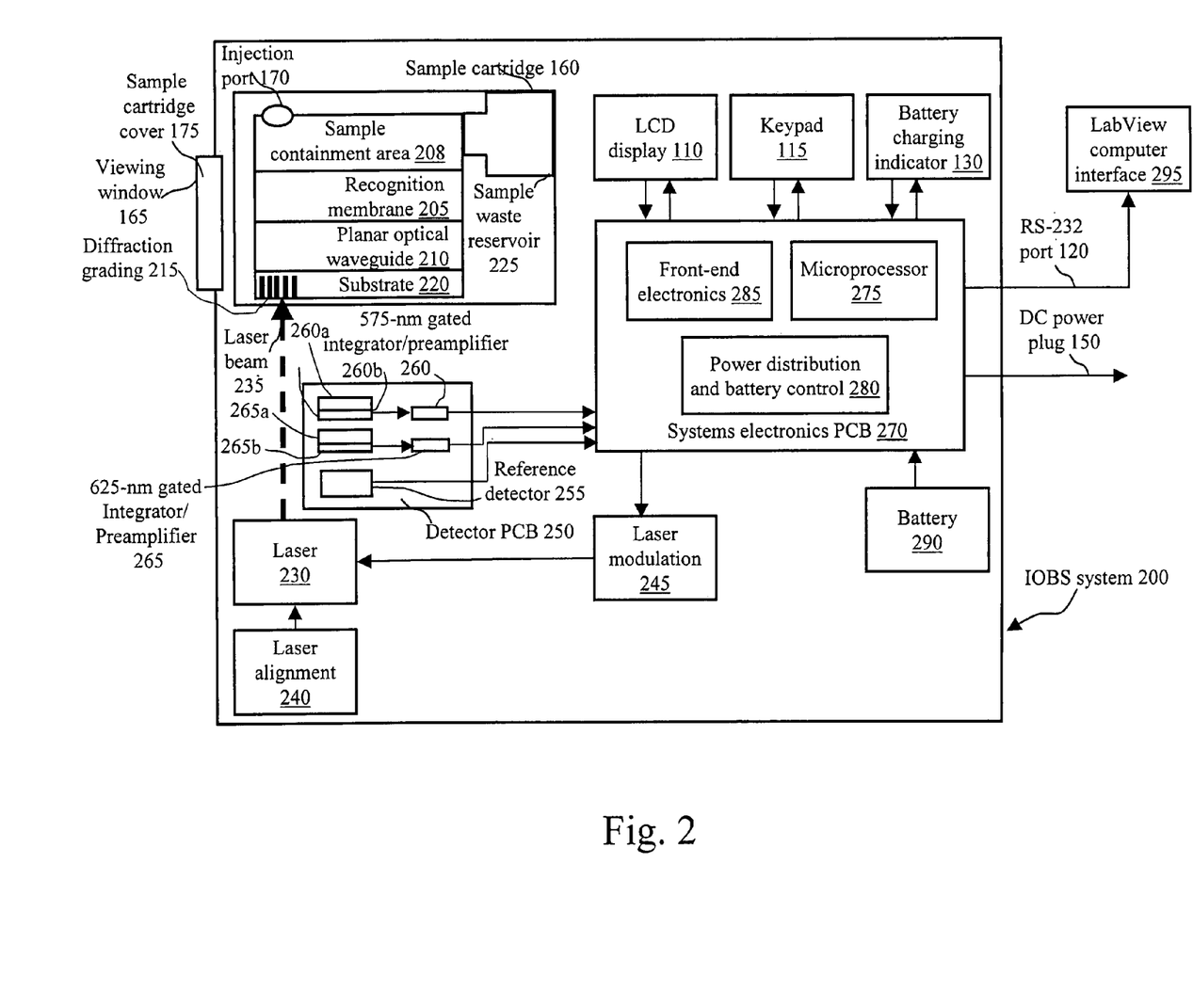
FIG. 2 is a block diagram of the overall integrated optical biosensor system.

FIG. 2 shows a block diagram of an IOBS system 200. IOBS system 200 includes sample cartridge 160, which further includes a recognition surface 205, a sample containment area 208, and a planar optical waveguide 210 (as described above). Recognition surface 205 is formed on the surface of planar optical waveguide 210, and includes receptive material selected to interact with certain biological, biochemical or chemical substances contained within a sample to be analyzed. For example, the receptive material may be natural or man made antibodies, antigens or chemical ligands. In one embodiment, recognition surface 205 can have a membrane such as a phospholipid bilayer (an organic two-layered membrane) to create an artificial cell surface. For implementation using a recognition membrane Natural or Man-made receptors for a specific protein are attached to the artificial cell surface using synthetic anchors. This is more specifically described in U.S. patent application Ser. No. 10/104,158, filed Mar. 21, 2002, by Schmidt et al. for "Generic Membrane Anchoring System," which is included herein for all purposes.

Conjugated to each man-made receptor is one of two kinds of reporter dye molecules: a donor fluorophore or and acceptor fluorophore. The membrane based assay is more specifically described in U.S. Pat. No. 6,297,059, issued Oct. 2, 2001, for "Triggered Optical Biosensor," which is included herein for all purposes. The membrane based assay using an optical waveguide as a transducer is more specifically described in U.S. patent application Ser. No. 09/598,882, filed Jun. 21, 2000, for "Optical Biosensor and Method for Detecting a Multivalent Target Molecule," which is included herein for all purposes. However, other recognition surfaces with receptive materials (or assays) that also produce fluorescent changes upon the binding of a targeted pathogen could be used as well. For example the recognition surface 205 may be comprised of a self-assembled monolayer (SAM) having man-made or natural receptors attached to the SAM surface using flexible length linkers with reporter dyes attached close to the receptors.

Planar optical waveguide 210 sits on a substrate 220 onto which diffraction grating 215 has been etched. A sample waste reservoir 225 is coupled to sample containment area 208. A laser 230 shines a laser beam 235 through the substrate 220 onto the diffraction grating 215. Laser 230 must be properly aligned via a laser alignment 240, using horizontal laser alignment wheel 140, and vertical laser alignment wheel 145. In order to efficiently couple laser beam 235 into planar optical waveguide 210 the angle of laser beam 235 with respect to diffraction grating 215 must match the resonant angle for excitation to occur so a minor adjustment of laser 230 with respect to planar optical waveguide 210 may be required. In the future, mass manufacture of waveguides with tight tolerances for waveguide and grating manufacture will eliminate the need for these adjustments. A laser modulation 245 controls power to laser 230. In one embodiment, laser 230 is an inexpensive, commercially available, 1-mW, 532-nm laser diode attenuated to 200 uW to reduce photo-bleaching of the reporter dyes and provide an eye-safe exposure/class IIIa laser. Other laser wavelengths may be used, and are determined by the excitation spectra of the fluorescent dyes selected. For example, 632-nm laser diodes may also be used with fluorescent dyes that can be excited by this wavelength. Laser 230 is also very low power and may be operated from a battery-sourced power supply.

Detector PCB 250 includes a reference detector 255, a 570-nm band pass filter 260a connected to silicon photodiode 260b that feeds to gated integrator/preamplifier 260, and a 632.8-nm band pass filter 265b connected to silicon photodiode 265b that feeds to gated integrator/preamplifier 265. Other bandpass filters may be used, and are selected according to the emission wavelength of the dyes selected for any particular application. The silicon photodiodes 260b, 265b may be a Hamamatsu S1227-16BR silicon photodiode, for example; however, the invention is not limited to that specific part, and one skilled in the art may substitute a similarly functioning device that is optimized for sensitivity in the visible range.

The information gathered by 632.8-nm gated integrator/preamplifier 265, 570-nm gated integrator/preamplifier 260, and reference detector 255 is delivered via signal wires to a system electronics PCB 270. System electronics PCB 270 includes a microprocessor 275, a power distribution and battery control 280, and front-end electronics 285. Front-end electronics 285 includes circuitry to receive analog light-intensity measurement information from detector PCB 250 and to amplify, filter, and convert the signals to a multi-bit, digital form that may then be processed by microprocessor 275.

Microprocessor 275 includes software to facilitate the functions of IOBS system 200. Having an internal controller saves space, allows the system to be portable, eliminates many compatibility and timing issues associated with external processing, and saves design time. Microprocessor 275 includes a CPU, memory, oscillator, watchdog timer, USART, and I/O interfaces incorporated within a single integrated circuit chip. In one embodiment, microprocessor 275 is a microcontroller, for example, a PIC 18C452. However, the invention is not limited to the use of a specific type of processor, and any suitable processing device may be used. For this example, microprocessor 275 has RAM available for variable storage and ROM for program storage. Microprocessor 275 controls all functions of IOBS apparatus 100 and is integrated with other hardware devices including, but not limited to, LCD display 110, keypad 115, and RS-232 port 120. Microprocessor 275 communicates serially with LCD display 110 using an RS-232 protocol.

In addition to inputs from keypad 115, IOBS apparatus 100 may also be coupled to PC software 295 via RS-232 port 120. The associated PC software 295 allows a user to implement all available functions without using keypad 115. This provides the user with a friendly PC GUI in a virtual push button fashion.

Therefore, IOBS apparatus 100 may be operated using keypad 115 and LCD display 120 on the front panel, or it may be operated using a serial interface to a PC running, for example, LABVIEW® 295 software. VISUAL BASIC® among other programs could also be used. (LABVIEW® is a software system that can be used). In addition to providing a GUI, computer interface 295 also provides the means for downloading all data that has been stored within the non-volatile memory of microprocessor 275. The data may then be processed using other traditional PC software applications.

Power distribution and battery control 280 functions to regulate the power supply to IOBS system 200. Since IOBS system 200 is designed to be portable, it is powered by an internal battery 290, such as a lithium-ion battery, when AC power is not available. Battery 290 provides stand-alone operation for up to six hours. An external AC/DC power supply plugged into DC power plug 150 may also be used at any time. A standard, commercially available 15-volt, 28-watt AC-to-DC converter (not shown) is used to provide DC power supply operation and recharge internal battery 290. Internal circuitry in power distribution and battery control 280 detects the presence of DC power plug 150 and automatically switches from battery power. Power distribution and battery control 280 charges internal battery 290 when DC power plug 150 is being used. Battery low indicator 125 illuminates when internal battery 290 is low. Battery charging indicator 130 is lit when internal battery 290 is charging. Battery charging indicator 130 turns off when internal battery 290 is fully charged.

Figure 3:
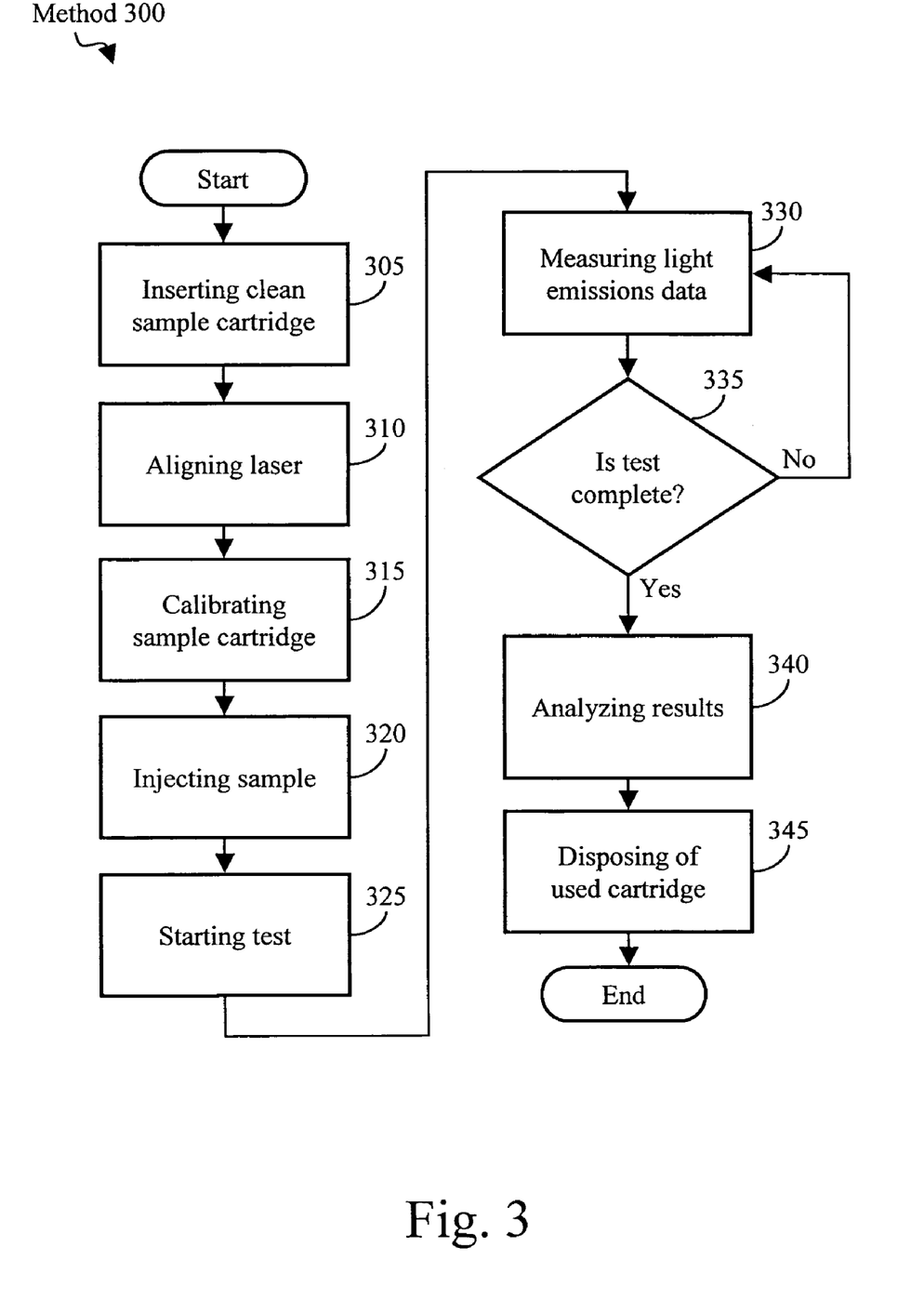
FIG. 3 illustrates an example method of operation for the integrated optical biosensor system.

The following method describes an example method of operation using IOBS apparatus 100:

FIG. 3 is a method 300 of operating IOBS apparatus 100 for a cholera toxin test sample.

Step 305: Inserting Clean Sample Cartridge

In this step, the operator inserts clean (i.e., not previously used for testing purposes) sample cartridge 160 into sample cartridge port 155 of IOBS apparatus 100. Method 300 proceeds to step 310.

Step 310: Aligning Laser

In this step, the user looks through viewing window 165 to ensure that laser beam 235 is properly aligned with diffraction grating 210 Using horizontal laser alignment wheel 140 and vertical laser alignment wheel 145, the user aligns laser 230 to the correct position indicated. To align the laser two methods may be used: (1) the user opens viewing window 165 and adjusts laser alignment wheels 140 and/or 145 to produce a streak of laser light parallel with the long dimension of viewing window 165. Laser alignment wheels 140 and/or 145 are adjusted until a maximum intensity is observed. (2) The user observes a numerical readout obtained from digitized signal intensity of reference detector 255 converted in microprocessor 275 to a numerical readout on the LCD display and adjusts laser alignment wheels 140 and/or 145 until a maximum value is obtained. Method 300 proceeds to step 315.

Step 315: Calibrating Sample Cartridge

In this step, the user selects "calibrate cell" either from the menu list on keypad 115 or from the GUI interface on a connected PC via computer interface 295. Each new sample cartridge 160 must be calibrated before an accurate test may be performed. Laser beam 235, now properly aligned, is coupled into planar optical waveguide 210 via diffraction grating 215 exciting recognition surface 205. Recognition surface 205 contains optically tagged receptors that are deposited on planar optical waveguide 210. The optical detection electronics on detector PCB 250 begin taking emission intensity readings from sample containment area 208. This provides a control basis for comparison of the fluorescence emission of the 575-nm and 625-nm dyes before and after the sample has been injected.

At present, the system operator is responsible for ensuring that a calibration step is performed for each new sample cartridge 160 inserted. However, automated methods of ensuring proper calibration of new sample cartridges 160 include a simple pressure switch that is installed into sample cartridge port 155 that sends a signal to microprocessor 275 when the sensor detects the removal of a sample cartridge 160 followed by the insertion of a new sample cartridge 160. This would indicate to system software that a calibration must be completed before testing may commence. Method 300 proceeds to step 320.

Step 320: Injecting Sample

Once laser 230 and sample cartridge 160 have been calibrated, IOBS apparatus 100 is ready to test the sample. The sample is injected into sample containment area 208 via injection port 170, forcing buffer fluid (not shown) in sample containment area 208 to be injected into sample waste reservoir 225. The buffer fluid is there to protect recognition surface 205 until such a time as a sample is injected. Sample waste reservoir 225 is a containment area that ensures that no hazardous materials leave hermetically sealed sample cartridge 160. Method 300 then proceeds to step 325.

Step 325: Starting Test

In this step, the user depresses the key on keypad 115 corresponding to "start test," or the user may select a "begin test" button on LabView computer interface 295. Current methods involve the user injecting the sample then depressing the correct keys on keypad 115 or LabView computer interface 295 to begin testing. Automated methods to determine sample injection include the use of a plunger device attached to sample waste reservoir 225 such that as sample waste reservoir 225 fills with buffer solution during injection when the plunger is displaced. Once sample waste reservoir 225 fills completely, the plunger is in a position to trigger either a position sensor or a pressure sensor that, in turn, marks time zero in microprocessor 275. Method 300 proceeds to step 330.

Step 330: Measuring Light Emissions Data

In this step, the filter electronics on detector PCB 250 begin taking emission intensity readings from sample containment area 208. Recognition surface 205 contains optically tagged receptors that are deposited on planar optical waveguide 210. Once recognition surface 205 has received the sample, laser beam 235 is coupled into optical planar waveguide 210, exciting recognition surface 205. In one embodiment, the binding of the targeted toxin to multiple receptors that are labeled with reporter dyes triggers fluorescent resonant energy transfer (FRET) to provide a change in fluorescence emission in the 575-nm and 625-nm dyes. The reduced emission in the 575-nm dye and the increased emission in the 625-nm dye is a measure of the concentration of bound toxin in recognition surface 205. Method 300 proceeds to step 335.

Step 335: Is Test Complete?

In this decision step, Method 300 checks to see if the test is complete. If yes, the test stops automatically and method 300 proceeds to step 340; if no, method 300 returns to step 330.

Step 340: Analyzing Results

In this step, IOBS apparatus 100 indicates the presence or absence of the target. If the target is detected, IOBS apparatus 100 indicates a concentration level. The IOBS detection algorithms in microprocessor 275 measure the change in relative intensities of fluorescence emission over time and determine the concentration of toxin based on the fluorescence change. It is understood that, although this embodiment uses the specific wavelengths of light mentioned herein, it is possible to design alternate embodiments of the IOBS that would use alternate reporter dyes requiring laser excitation of a different wavelength, that, in turn, would result in fluorescence emissions of different wavelengths. Method 300 proceeds to step 345.

Step 345: Disposing of Used Cartridge

In this step, the user ejects sample cartridge 160 and disposes of it in a medical waste receptacle. Method 300 is therefore ended.

Figure 4A:
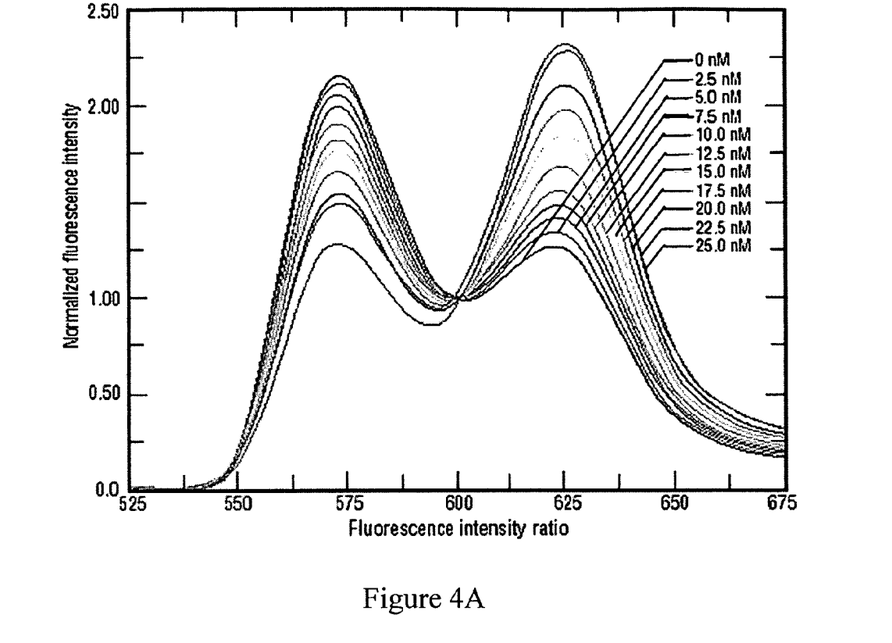
FIG. 4A is data measured using the IOBS sample cartridge and a commercial fiber optic spectrometer for detection. The spectral curves measured by the fiber optic spectrometer illustrate the relative changes in emission intensity of the 575-nm wavelength yellow fluorescent dye and the 625-nm wavelength red fluorescent dye in response to successive injections of 2.5 nM cholera toxin.
Figure 4B:
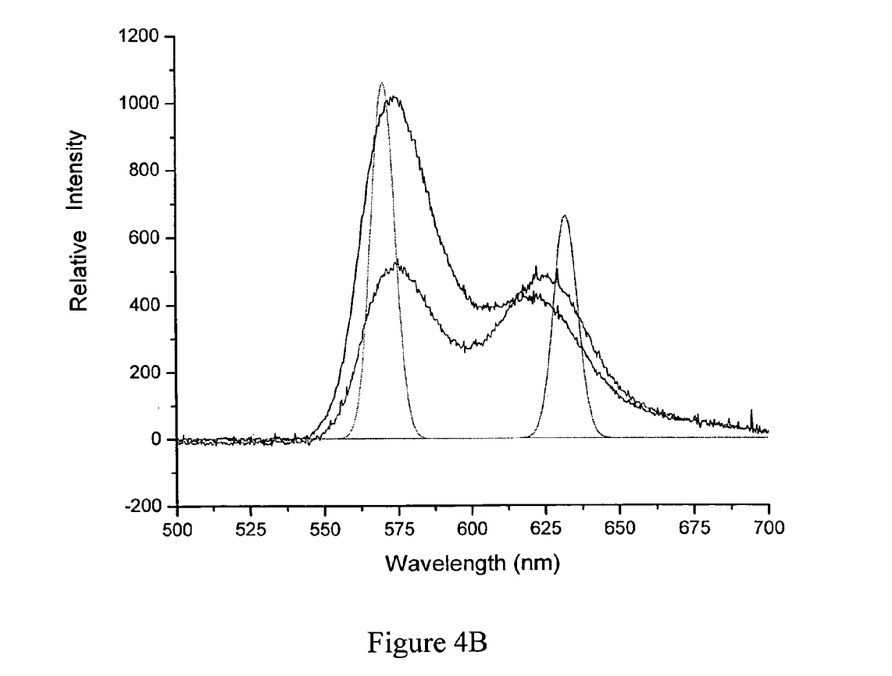
FIG. 4B shows IOBS apparatus 100 bandpass filter relationship to the spectra. IOBS apparatus 100 measures the filtered detector responses and does not measure the entire spectra. In this embodiment the use of filtered detectors was selected over a fiber optic spectrometer to provide for a reduction both in instrument size and cost.

FIG. 4A and FIG. 4B are graphs that further explain the emission comparisons. The graphs depict the results of a typical cholera toxin detection test using IOBS apparatus 100. The graphs are different representations of the measured fluorescence output of the sample cell in response to successive injections of 2.5 nM solutions of cholera toxin.

FIG. 4A is data measured using the IOBS sensor cartridge and a commercial fiber optic spectrometer depicting the relative changes in intensity of the evanescence of the 575-nm wavelength yellow fluorescent dye and the 625-nm wavelength red fluorescent dye. The relative intensity of the 575-nm wavelength decreases with successive injections of 2.5 nM cholera toxin while the relative intensity of the 625-nm wavelength increases, showing the presence of cholera toxin in the sample.

FIG. 4B shows IOBS apparatus 100 bandpass filter relationship to the spectra. IOBS apparatus 100 measures the filtered detector responses and does not measure the entire spectra. In this embodiment the use of filtered detectors was selected over a fiber optic spectrometer to provide for a reduction both in instrument size and cost.

Figure 4C:
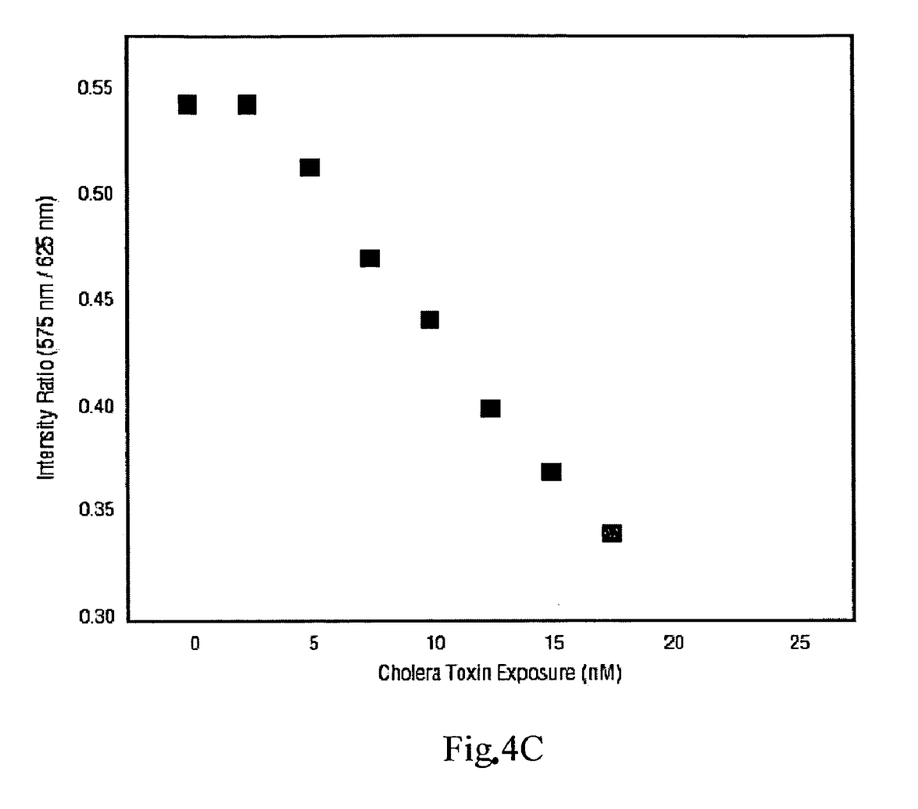
FIG. 4C shows IOBS apparatus 100 bandpass filter relationship to the spectra. IOBS apparatus 100 measures the filtered detector responses and does not measure the entire spectra.

FIG. 4C is a graph of the ratio of yellow wavelength intensity to red wavelength intensity as measured by the IOBS instrument resulting from successive injections of 2.5 nM solutions of cholera toxin.

In summary, the present invention provides a hand-held, portable, battery-operated, simple, and inexpensive device and method for detecting the presence of toxins, in this case a cholera toxin, in a timely manner. The detection of cholera takes approximately five minutes using IOBS apparatus 100. In emergency situations, this timesaving may be extremely important. It is also important to note that no added reagents, washing, mixing, agitating, or any other type of chemical processing was necessary to complete the test. A user inserts a clean sample cartridge 160 into IOBS apparatus 100. Sample cartridge 160 is then calibrated and the sample is injected via injection port 170.

The test begins at the press of a button and completes in fewer than ten minutes. The user simply disposes of the used cartridge in a medical waste receptacle. No other processing or waiting is required and the results are very accurate, since there has been little opportunity for the introduction of errors. The tests may be completed in the field or in other uncontrolled environments. When battery power begins to diminish, battery low indicator 125 notifies the user. DC power may be used instead of battery power. Battery 290 is recharged automatically using DC power plug 150 for ease of maintenance and to ensure future operation of IOBS apparatus 100.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An integrated optical biosensor comprising:
   a first enclosure;
   a pathogen recognition surface, including a planar optical waveguide and grating located in said first enclosure;
   an aperture in said first enclosure for insertion of sample to be investigated to a position in close proximity to said pathogen recognition surface;
   a second enclosure releasably attached to said first enclosure;
   a laser in said second enclosure including mechanical adjustment wheels for aligning and means for modulating said laser, said laser having its light output directed toward said grating;
   detection means located in said second enclosure and in optical communication with said pathogen recognition surface for detecting pathogens after interrogation by said laser light and outputting said detection;
   electronic means located in said second enclosure receiving said detection for processing said detection, and outputting information on said detection;
   and an electrical power supply located in said second enclosure for supplying power to said laser, said detection means and said electronic means.

2. The apparatus as described in claim 1, further comprising an input key pad and liquid crystal display in said enclosure.

3. The apparatus as described in claim 1, wherein said electronic means comprises front end electronics, a microprocessor, and a power distribution control.

4. The apparatus as described in claim 1, wherein said electrical power supply is a rechargeable battery.

5. The apparatus as described in claim 4, wherein said electrical power supply is an AC to DC converter for supplying power and charging said rechargeable battery.

6. The apparatus as described in claim 1, further comprising a RS-232 port for connecting said electronic means to a computer interface.

7. The apparatus as described in claim 1, wherein said modulation of said laser involves controlling power provided to said laser.

8. The apparatus as described in claim 1, wherein said pathogen recognition surface comprises a phospholipid bilayer having man-made receptors for a specific protein attached using synthetic anchors, with either a donor fluorophore or an acceptor fluorophore conjugated to each of said man-made receptors.

9. The apparatus as described in claim 1, wherein said pathogen recognition surface is comprised of a self-assembled monolayer (SAM) having man-made or natural receptors attached to the SAM surface using flexible length linkers with reporter dyes attached close to the receptors.

10. The apparatus as described in claim 1, wherein said first enclosure is in optical communication with said second enclosure.

11. An integrated optical biosensor comprising:
    a first enclosure;
    a pathogen recognition surface, including a planar optical waveguide and grating located in said first enclosure;
    an aperture in said first enclosure for insertion of sample to be investigated to a position in close proximity to said pathogen recognition surface;
    a second enclosure releasably attached to said first enclosure;
    a laser in said second enclosure including means for aligning and means for modulating said laser, said laser having its light output directed toward said grating, wherein said laser is a 1-mW, 532-nm laser diode attenuated to 200 µW;
    detection means located in said second enclosure and in optical communication with said pathogen recognition surface for detecting pathogens after interrogation by said laser light and outputting said detection;
    electronic means located in said second enclosure receiving said detection for processing said detection, and outputting information on said detection; and an electrical power supply located in said second enclosure for supplying power to said laser, said detection means and said electronic means.

12. The apparatus as described in claim 11, further comprising an input key pad and liquid crystal display in said enclosure.

13. The apparatus as described in claim 11, wherein said electronic means comprises front end electronics, a microprocessor, and a power distribution control.

14. The apparatus as described in claim 11, wherein said electrical power supply is a rechargeable battery.

15. The apparatus as described in claim 14, wherein said electrical power supply is an AC to DC converter for supplying power and charging said rechargeable battery.

16. The apparatus as described in claim 11, further comprising a RS-232 port for connecting said electronic means to a computer interface.

17. The apparatus as described in claim 11, wherein said modulation of said laser involves controlling power provided to said laser.

18. The apparatus as described in claim 11, wherein said pathogen recognition surface comprises a phospholipid bilayer having man-made receptors for a specific protein attached using synthetic anchors, with either a donor fluorophore or an acceptor fluorophore conjugated to each of said man-made receptors.

19. The apparatus as described in claim 11, wherein said pathogen recognition surface is comprised of a self-assembled monolayer (SAM) having man-made or natural receptors attached to the SAM surface using flexible length linkers with reporter dyes attached close to the receptors.

20. The apparatus as described in claim 11, wherein said first enclosure is in optical communication with said second enclosure.

* * * * *